(12) United States Patent
Boese et al.

(10) Patent No.: US 7,787,941 B2
(45) Date of Patent: Aug. 31, 2010

(54) MEDICAL EXAMINATION AND/OR TREATMENT SYSTEM

(75) Inventors: Jan Boese, Eckental (DE); Martin Kleen, Furth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 1104 days.

(21) Appl. No.: 11/378,060

(22) Filed: Mar. 17, 2006

(65) Prior Publication Data

US 2006/0241415 A1 Oct. 26, 2006

(30) Foreign Application Priority Data

Mar. 18, 2005 (DE) .................. 10 2005 012 696

(51) Int. Cl.
*A61B 5/04* (2006.01)
(52) U.S. Cl. .................................... 600/509
(58) Field of Classification Search .............. 607/5, 607/29, 30, 31; 600/508, 509, 510, 523, 600/429, 407, 417; 606/130; 378/205
See application file for complete search history.

(56) References Cited

U.S. PATENT DOCUMENTS

| 4,576,178 | A | * | 3/1986 | Johnson ...................... 600/483 |
| 4,792,145 | A | * | 12/1988 | Eisenberg et al. ........... 600/528 |
| 5,246,005 | A | | 9/1993 | Carroll et al. |
| 5,732,704 | A | | 3/1998 | Thurston et al. |
| 5,868,680 | A | * | 2/1999 | Steiner et al. ............... 600/518 |
| 5,891,180 | A | * | 4/1999 | Greeninger et al. ........... 607/32 |
| 6,083,163 | A | * | 7/2000 | Wegner et al. .............. 600/429 |
| 6,368,285 | B1 | * | 4/2002 | Osadchy et al. ............. 600/508 |

FOREIGN PATENT DOCUMENTS

| EP | 0 637 934 B1 | 7/2000 |
| EP | 0 894 473 B1 | 11/2003 |
| WO | WO 97/23172 A2 | 7/1997 |
| WO | WO 98/31280 | 7/1998 |
| WO | WO 2005/009215 A2 | 2/2005 |

* cited by examiner

*Primary Examiner*—Mark W Bockelman
*Assistant Examiner*—Elizabeth K So

(57) ABSTRACT

Medical examination and/or treatment system, configured to capture and output at least one parameter to be monitored during examination and/or treatment, with the system being configured to evaluate the at least one captured parameter and to output an acoustic signal that can be modified as a function of the result of the evaluation.

19 Claims, 1 Drawing Sheet

MEDICAL EXAMINATION AND/OR TREATMENT SYSTEM

CROSS REFERENCE TO RELATED APPLICATIONS

This application claims priority to the German Application No. 10 2005 012 696.0, filed Mar. 18, 2005 which is incorporated by reference herein in its entirety.

FIELD OF INVENTION

The invention relates to a medical examination and/or treatment system, configured to capture and output at least one parameter to be monitored during the examination and/or treatment.

BACKGROUND OF INVENTION

Conventional medical devices and systems generally have a display, to display specific information for the user. In the simplest instance this can be light-emitting diodes but medical devices are also known that can display parameters in the form of numerical values. These can be seven-segment displays or even bigger displays, for example using a screen. Other optical display options are also known, such as bar diagrams to display parameters.

SUMMARY OF INVENTION

The optical displays of the known medical examination or treatment systems have become more complex over time and require the attention of the user to an increasing degree. In the case of certain monitored parameters, the user of the device or system, generally the doctor carrying out the treatment, must monitor one or more parameters continuously, forcing said doctor to look away from the examination or operation area.

The invention therefore addresses the problem of specifying a medical examination and/or treatment system, which facilitates the monitoring of one or more parameters.

To resolve this problem, provision is made with a medical examination and/or treatment system of the type mentioned above, for the system to be configured to evaluate the at least one captured parameter and to output an acoustic signal that can be modified as a function of the result of the evaluation.

The invention is based on the knowledge that one or more parameters, which are generally displayed optically, are supplied to the user additionally or alternatively in an acoustic manner. To this end the invention provides for an acoustic signal to be output, which can be modified as a function of the current value of the parameter. Before it is output, the parameter undergoes an evaluation and the result of the evaluation is then output acoustically. Compliance with one or more predefined conditions can also be verified as part of the evaluation. In the simplest instance it can be verified whether the current value of the parameter is above or below a threshold value. The result of this evaluation is either "yes" or "no", with a separate acoustic signal being assigned to one or both results, which is then output.

In a further embodiment of the invention the acoustic signal can be a polyphonic tone. A polyphonic tone allows a number of parameters to be output together. At least one captured parameter can thereby be assigned to each individual tone of the polyphonic tone. Three tones can be used to output three different monitored parameters as a polyphonic tone, with the three tones expediently forming a triad. If one of the parameters changes, this causes the individual tone assigned to the respective parameter to be modified, resulting in a corresponding modification of the polyphonic tone, which is perceived immediately by the user of the claimed examination and/or treatment system. With practice the user can even identify which parameter has changed.

It is also within the scope of the invention that it can be determined as part of the evaluation whether a parameter is within or outside a permissible value range. To this end it is verified, in addition to the above-mentioned verification of whether a threshold value is exceeded, whether the parameter is above or below a second threshold value. The two threshold values form upper and lower limits for the parameter.

The tone level of the acoustic signal can be modified, if the respective parameter is outside its permissible value range. If there are a number of parameters, with an individual tone assigned to each, a specific value range can be defined for each parameter.

According to the invention different options are provided to modify the acoustic signal if a parameter is outside the permissible value range. In one variant the duration of the acoustic signal is modified. Such a modification can be perceived and interpreted as a parameter deviation very easily. In another variant the volume of the acoustic signal is modified. A parameter deviation can then be signaled by an increase in volume.

It is also within the scope of the invention for the acoustic signal to be output as an interrupted signal. If the acoustic signal is a polyphonic tone, at least one individual tone can be output interrupted.

According to a particularly preferred embodiment of the invention, the system can be an electro-physiological mapping or ablation system. The parameter to be monitored can then be the contact between a catheter and a part of the body to be examined. The position of the catheter in particular can be the parameter to be monitored, optionally also the change over time, i.e. the derivation of the position. Alternatively or additionally the parameter to be monitored can be the voltage of an electrocardiogram (ECG) derived at the catheter site, optionally also the change in it over time. It is also possible for the parameter to be monitored to be the length of the cardiac cycle, optionally also the change in it over time. Finally the so-called local activation time can also be monitored or the change in it over time. All these parameters provide information about the quality of the wall contact between the catheter, which can be an ablation catheter, and the corresponding body tissue, for example the endocardial tissue. During ablation procedures it is essential for the ablation catheter to have the best possible contact with the endocardial tissue, so that the radio frequency can be output to the tissue in a defined manner and the intended lesion can be positioned in a defined manner. The acoustic signaling of the quality of the wall contact provided for by the invention allows the user to monitor wall contact continuously without having to look at a display.

According to a further, also particularly preferred, embodiment of the invention, the system is configured to register or merge at least two images. The term registering generally refers to the combining of at least two images from different sources, for example one image from a magnetic resonance examination and one image from a computed tomography examination. Ultrasound images or 3-D rotational angiography images can also be registered.

According to the invention the examination and/or treatment system can be used for offline registering or online registering. Offline registering is carried out before the actual intervention, while online-registering takes place during an intervention. Initially 3-D images are registered with other 3-D images, but it is also possible to register 3-D images with 2-D images.

According to the invention the parameter to be monitored can be the registering error of the claimed examination and/or treatment system.

It is also possible for the claimed examination and/or treatment system to be configured to carry out a registering process to control a navigated device, in particular a catheter or a surgical tool. Information about the position of the device is thereby registered with 3-D image information, to display the device in three-dimensional space. The distance between the navigated device and a part of the body to be examined is preferably the parameter to be monitored. The distance between a surgical instrument and an anatomical structure or a functional area or an operation planning path can also be used as the parameter to be monitored. With all the embodiments the parameter(s) to be monitored is/are evaluated and the output acoustic signal is modified if a threshold value or a value range is exceeded.

BRIEF DESCRIPTION OF THE DRAWINGS

Further advantages and details of the invention are described in more detail below with reference to the figures. The figures are schematic diagrams, in which.

DETAILED DESCRIPTION OF INVENTION

Figure 1:
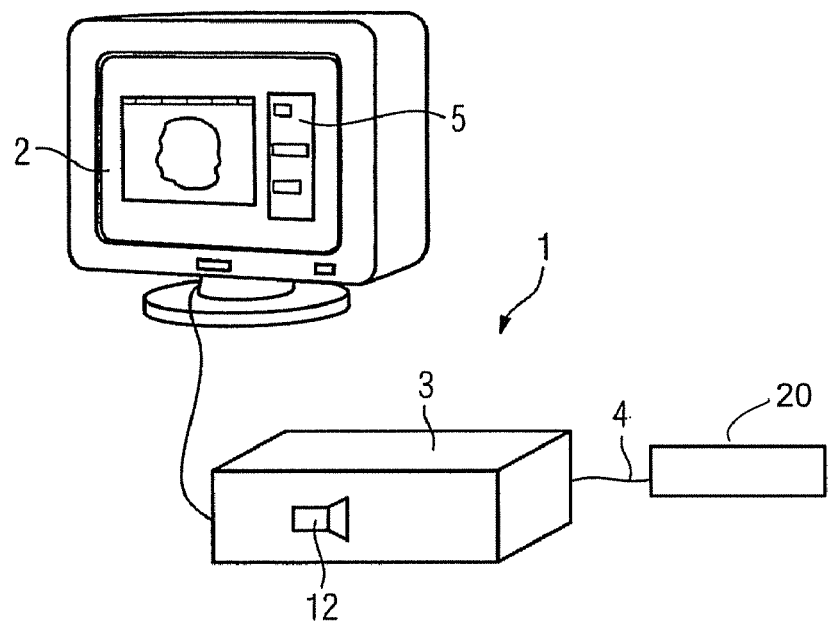
FIG. 1 shows a first exemplary embodiment of a claimed medical examination system.

FIG. 1 shows a schematic diagram of a medical examination and treatment system with its most important components, configured in this exemplary embodiment as a mapping and ablation system 1. These systems are used in electrophysiology to carry out ablation procedures. The mapping and ablation system 1 has a display 2, on which for example the examination area and parameters to be monitored are displayed. Adjustments made are also displayed.

The display is connected to a computer 3 operating as the computing and evaluation device, to which an ablation catheter 20 is also connected via a cable connection 4.

At the time of the ablation it is important for the ablation catheter to have the best possible direct contact with the endocardial tissue, in order to output the radio frequency to the tissue in a defined manner and to position the lesion in a defined manner. It is therefore necessary to capture and display the "quality" of the wall contact, which is specified by defined parameters, during the procedure.

Parameters, which specify the quality of the wall contact, are essentially parameters, which characterize the stability of the state of the catheter or the anatomy of the heart or another part of the body under examination: It is important for the parameter to be captured at a defined point in time of the cardiac cycle. The examination and/or treatment system 1 can capture the following parameters in particular: stability of the position of the ablation catheter over time, stability of the voltage of a derived intracardiac electrocardiogram (ECG) at the current site of the ablation catheter over time, stability of the length of the cardiac cycle and stability of the so-called local activation time over time. The parameter local activation time provides information about maximum propagation values at a defined point in time.

As with conventional mapping and ablation systems, the system 1 displays the quality of the wall contact for every cardiac cycle as a bar diagram 5 on the display 2. The operator must therefore also keep an eye on the various parameters of the quality of the wall contact as well as the images of the examination area, the ECG derivations and other output variables for each radio frequency output that are similarly displayed. As this is not always possible for the user during a procedure that often lasts a number of hours, the system 1 is configured to evaluate the parameters and to output an acoustic signal. The computer 3 carries out the evaluation and a speaker 12 is provided to output the acoustic signal. The acoustic signal can thereby be modified as a function of the result of the evaluation.

In the exemplary embodiment shown the parameters "position of the ablation catheter", "voltage of the derived intracardiac electrocardiogram" and "stability of the cardiac cycle lengths" are taken into account. A permissible value range is thereby assigned to each of these parameters, defined by a lower and upper limit value. As part of the evaluation of the parameters it is verified whether a specific parameter is within or outside its permissible value range. The acoustic signal is a polyphonic tone, with one of the three parameters assigned to each individual tone of the polyphonic tone. This relationship is shown in FIG. 2.

Figure 2:
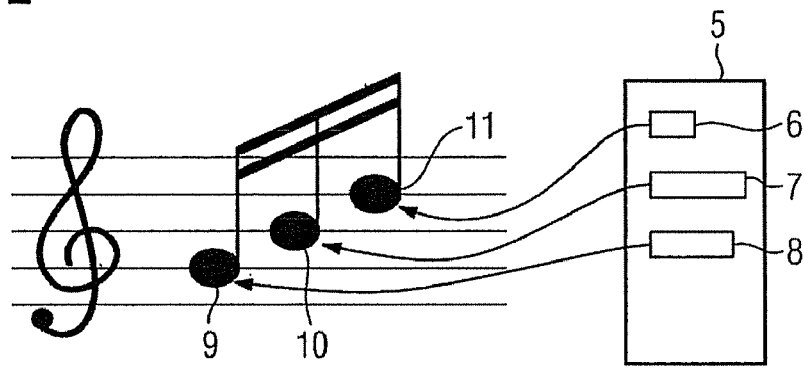
FIG. 2 shows the modification of an acoustic signal as a function of parameters.

FIG. 2 shows the modification of the acoustic signal as a function of monitored parameters.

FIG. 2 shows an enlargement of the bar diagram 5, which is displayed on the display 2. The bar diagram 5 includes three parameters 6, 7, 8, with an individual tone 9, 10, 11 assigned to each. The intervals between the tones 9 and 10 or 10 and 11 comprise a minor third or a major third, such that the tones 9, 10, 11 together form a major triad.

This polyphonic tone is output via the speaker 12 of the computer 3. The polyphonic tone codes the parameters 6, 7, 8, which contain information about the quality of the wall contact of the ablation catheter. Other exemplary embodiments can of course also use other parameters but in general any number of parameters that are of relevance in electro-physiological procedures can be coded by the described acoustic coding and output as an acoustic signal.

If all the parameters are within their valid value ranges, the user h ears a harmonic tone. If the output acoustic signal sounds discordant or "strange", this tone deviation is an indication that the quality of the wall contact has deteriorated. The user must then take steps to improve the wall contact of the ablation catheter.

In a modified embodiment three tones are overlaid, which are normally identical and only differ if there is deviation from a normal value or the value range has been left. In the case of minor deviations, these modifications can be distinguished very easily from the monophonic normal.

The triad shown schematically in FIG. 2 can be overlaid with noise in another variant.

The triad can also be interrupted or individual tones can be interrupted. It is of course also possible to modify the length of the triad or the length of individual tones for coding purposes. In this context it is also possible to modify the volume of the triad or individual tones.

If more than three parameters are to be taken into account, a combination of five tones or nine tones can be used instead of a triad, until the limits of the power of the human ear to distinguish are reached.

The medical examination and treatment system shown in FIGS. 1 and 2 means that the user no longer has to monitor parameters visually on a continuous basis during an electrophysiological procedure, in that the parameters displayed separately on the display 2 undergo an evaluation and the result of the evaluation is output as a modifiable acoustic signal.

Figure 3:
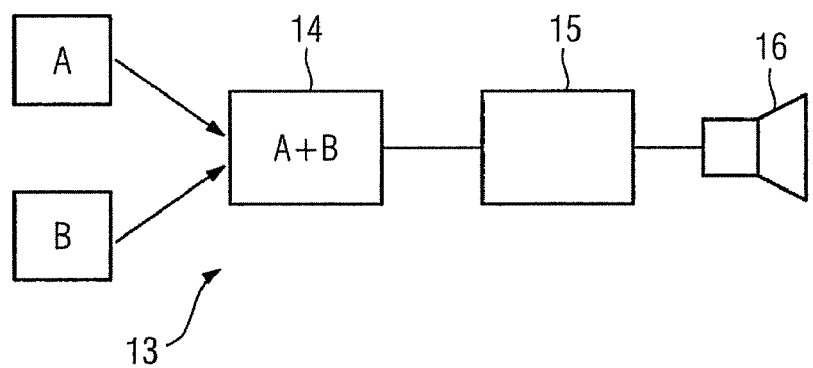
FIG. 3 shows a second exemplary embodiment of a claimed medical examination system.

FIG. 3 shows a second exemplary embodiment of the invention.

An examination and treatment system 13 is able to register two three-dimensional images A, B for diagnostic purposes. During certain examinations images are available from different sources. In the exemplary embodiment shown the image A is produced by means of a magnetic resonance examination (MR) and the image B is generated by computed tomography (CT).

The system shown in FIG. 3 operates in principle with any two three-dimensional images. For example ultrasound images, images from 3-D rotational angiography and SPECT/PET images could also be registered.

When two images or image data records are registered, the user has to be informed continuously about the current quality of the registering process. With conventional examination and treatment systems there is optical feedback, for example in the form of a screen display. To avoid the disadvantage of the user having to look away from the examination or operation area, with the examination and treatment system 13 shown in FIG. 3, after registering 14 an evaluation process 15 takes place, to determine the quality of the registering process. The quality of the registering process can thereby be captured as a deviation from an optimum value. After the evaluation 15 an acoustic signal is output via a speaker 16. As with the first exemplary embodiment described above, a permissible value range can be defined for the registering error, with the signal being modified if this is exceeded. The user then identifies a signal modification as a deviation from a normal value and can take corresponding steps. As with the first exemplary embodiment the acoustic signal can be modified in different ways. For example it can be interrupted, the signal length can be modified, the tone level can be modified or the signal can be overlaid with a noise signal.

In the case of applications with registering processes in particular, in which registering operates at the same time as a medical intervention on a patient, acoustic feedback about the quality of the registering process is expedient, so that the user can concentrate on the medical intervention, without having to keep an eye on optical displays. Up to a certain threshold the acoustic signal sounds harmonic, thereby indicating an acceptable registering error. If this threshold is exceeded, the acoustic signal becomes less and less harmonic, the further the registering error deviates from the threshold value.

The exemplary embodiment shown in FIG. 3 can be implemented both with offline registering and with online registering.

The invention can also be used to guide navigated devices such as catheters or navigated surgical tools in 3-D images. In this instance it is important to monitor the distance between navigated devices or surgical instruments and anatomical structures or functional areas or operation planning paths. In particular in the case of minimally invasive interventions such as vascular interventions or in the case of minimally invasive interventions in neurosurgery or in the case of abdominal interventions, medical devices with optical or electromagnetic position sensors are used. This allows the navigated devices to be superimposed in a 3-D anatomical visualization after registering. The position and orientation of the ablation catheter are visualized during the procedure. If the catheter is displayed outside the anatomical surface, this is due either to a registering error or an insufficiently precise display of the electro-anatomical map or in the worst instance perforation of the cardiac wall, of which the user is notified by the modifiable acoustic signal.

In minimally invasive neurosurgery instruments are introduced into the patient's brain through the smallest possible access point and guided with the aid of images, for example by means of CT, MR, 3D rotational angiography or 3-D ultrasound data. Certain areas of relevance such as a tumor to be removed, a functional center that must not be damaged, etc. are thereby often known. In this instance the distance between the navigated instrument and these relevant anatomical or functional structures can be coded acoustically in real time and transmitted to the user as acoustic feedback.

The invention claimed is:

1. A medical examination or treatment system, comprising:
an acquisition unit for acquiring at least one electrocardiogram parameter and at least a second parameter to be monitored during an examination or treatment;
an output unit for outputting the acquired parameters; and
an evaluation unit for evaluating the acquired parameters such that the acquired parameters are output by the output unit as an acoustic signal, wherein the acoustic signal is a polyphonic tone having a plurality of individual tones, each tone representing one of said electrocardiogram or second parameters and at least one property of the acoustic signal is adjusted based on the evaluated parameters.

2. The system according to claim 1, wherein the polyphonic tone is a triad or a chord.

3. The system according to claim 1, wherein the evaluation unit is configured to evaluate each of the acquired parameters relative to a parameter range.

4. The system according to claim 3, wherein adjusting the acoustic signal includes adjusting a pitch of the acoustic signal if at least one of the acquired parameters falls outside the parameter range.

5. The system according to claim 3, wherein adjusting the acoustic signal includes adding noise to the acoustic signal if at least one of the acquired parameters falls outside the parameter range.

6. The system according to claim 3, wherein adjusting the acoustic signal includes adjusting a duration or a volume of the acoustic signal if at least one of the acquired parameters falls outside the parameter range.

7. The system according to claim 3, wherein adjusting the acoustic signal includes interrupting the output of the acoustic signal if at least one of the acquired parameters falls outside the parameter range.

8. The system according to claim 3, wherein the acoustic signal is adjusted if at least one of the acquired parameters falls outside the parameter range.

9. The system according to claim 3, wherein the system is an electro-physiological mapping or ablation system.

10. The system according to claim 9, wherein at least one of the acquired parameters represents a physical contact between a catheter of the system and a part of a body under examination or treatment.

11. The system according to claim 9, wherein at least one of the acquired parameters represents a position or a change of position of a catheter of the system.

12. The system according to claim 9, wherein at least one of the acquired parameters is a voltage or a change of voltage of an electrocardiogram acquired at a position of a catheter of the system.

13. The system according to claim 9, wherein at least one of the acquired parameters is a length or a change of length of a cardiac cycle.

14. The system according to claim 9, wherein at least one of the acquired parameters is the Local Activation Time or a change of the Local Activation Time.

15. The system according to claim 1, wherein the system is configured to register or merge at least two images with each other.

16. The system according to claim 15, wherein at least one of the acquired parameters is a registering error.

17. The system according to claim 1, wherein the system is configured to register at least two images with each other for controlling a navigated medical intervention device.

18. The system according to claim 17, wherein at least one of the acquired parameters is a distance between the navigated device and a part of a body under examination or treatment or a distance between the navigated device and a further navigated medical intervention device.

19. A method of acquiring and outputting at least one parameter and at least a second parameter to be monitored during an examination or treatment, comprising:

acquiring the at least one parameter during an electrocardiogram examination;

acquiring the at least second parameter;

evaluating the acquired parameters;

outputting the acquired parameters as individual tones of a polyphonic acoustic signal, wherein at least one property of the acoustic signal is adjusted based on the evaluated parameters, the at least one property comprising one of the group consisting of noise added to the acoustic signal, and an interruption of the output of the acoustic signal.

* * * * *